United States Patent
Sherman et al.

(10) Patent No.: US 6,328,854 B1
(45) Date of Patent: Dec. 11, 2001

(54) METHOD OF AND APPARATUS FOR MANUFACTURING METHANOL

(75) Inventors: Jeffrey H. Sherman, Dallas, TX (US); Philip Grosso, Auburn, CA (US)

(73) Assignee: GRT, Inc., The Woodlands, TX (US)

( * ) Notice: Subject to any disclaimer, the term of this patent is extended or adjusted under 35 U.S.C. 154(b) by 0 days.

(21) Appl. No.: 09/522,982

(22) Filed: Mar. 10, 2000

Related U.S. Application Data

(63) Continuation-in-part of application No. 09/370,945, filed on Aug. 9, 1999, now Pat. No. 6,156,279, which is a division of application No. 09/224,394, filed on Dec. 31, 1998, now Pat. No. 6,129,818, which is a continuation-in-part of application No. 09/058,494, filed on Apr. 10, 1998, now Pat. No. 5,954,925.

(51) Int. Cl.[7] .................................................. C07C 29/48
(52) U.S. Cl. ....................................................... 204/157.9
(58) Field of Search ............................ 204/157.6, 157.9; 422/186.3; 210/748, 763

(56) References Cited

U.S. PATENT DOCUMENTS 5,779,912 * 7/1998 Gonzalez-Martin et al. .... 422/186.3
6,156,211 * 12/2000 Gonzalez-Martin et al. .... 422/186.3

* cited by examiner

*Primary Examiner*—Kathryn Gorgos
*Assistant Examiner*—Thao Tran
(74) *Attorney, Agent, or Firm*—Michael A. O'Neil

(57) ABSTRACT

A porous tube is positioned coaxially around and in axial alignment with a tubular lamp forming an annulus therebetween. Methane is directed through the porous tube and forms submicron size bubbles in a liquid flowing through the annulus. Energy from the tubular lamp generates hydroxyl radicals in the liquid which combine with the methane to form methanol. Photocatalytic material may be provided in the annulus either in the form of a layer of photocatalytic material formed on the interior surface of the porous tube or in the form of particles of photocatalytic material circulating through the annulus with the flowing liquid. A heat transfer apparatus may be provided in the annulus for removing heat generated by operation of the lamp.

6 Claims, 8 Drawing Sheets

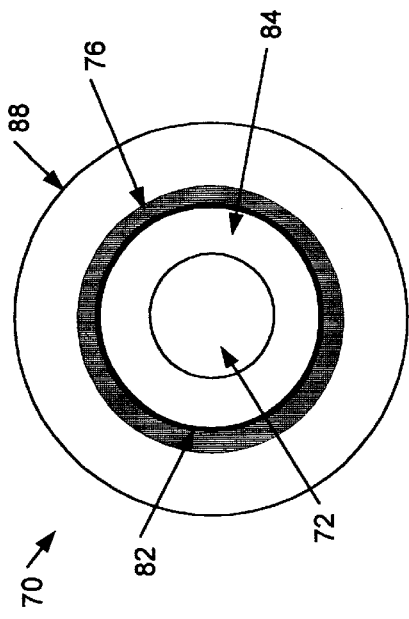
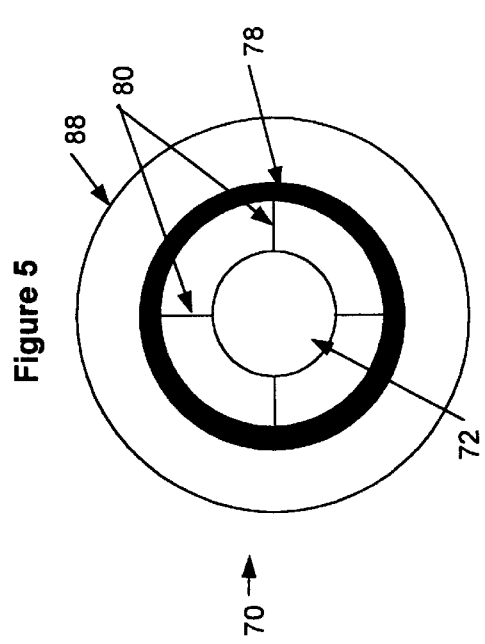
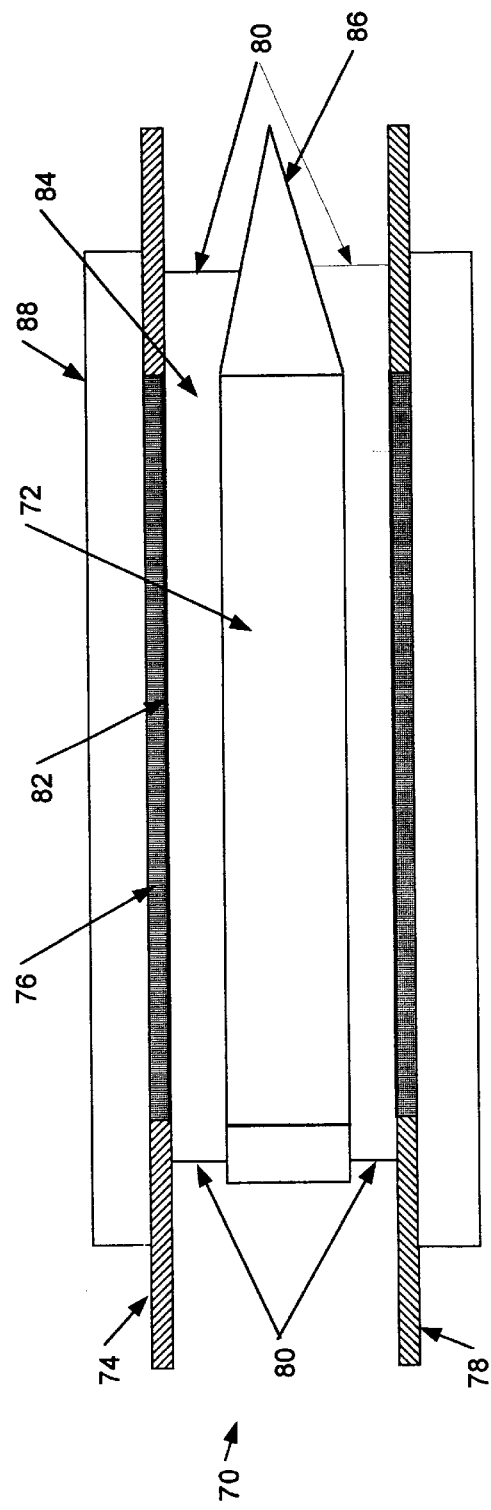

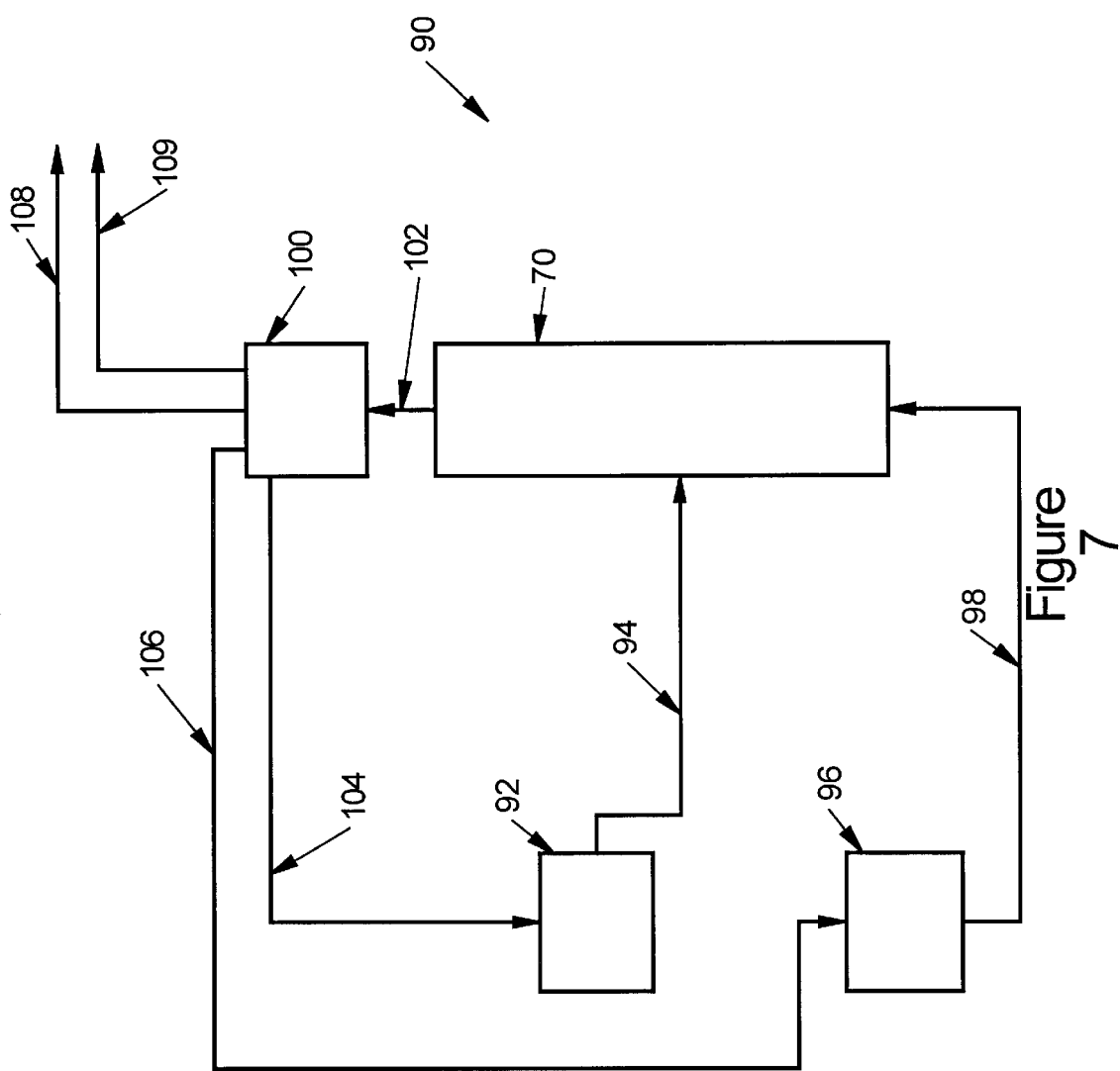

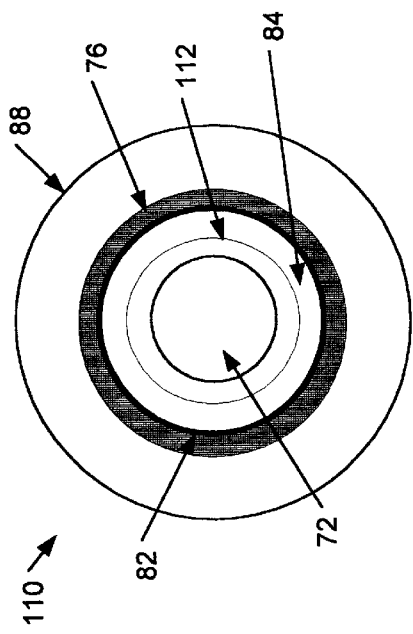
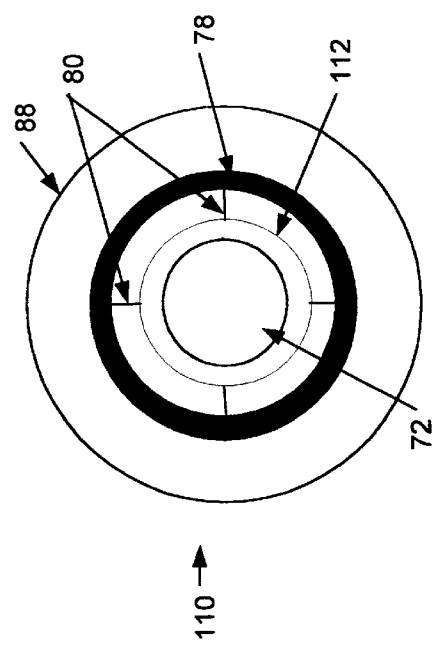
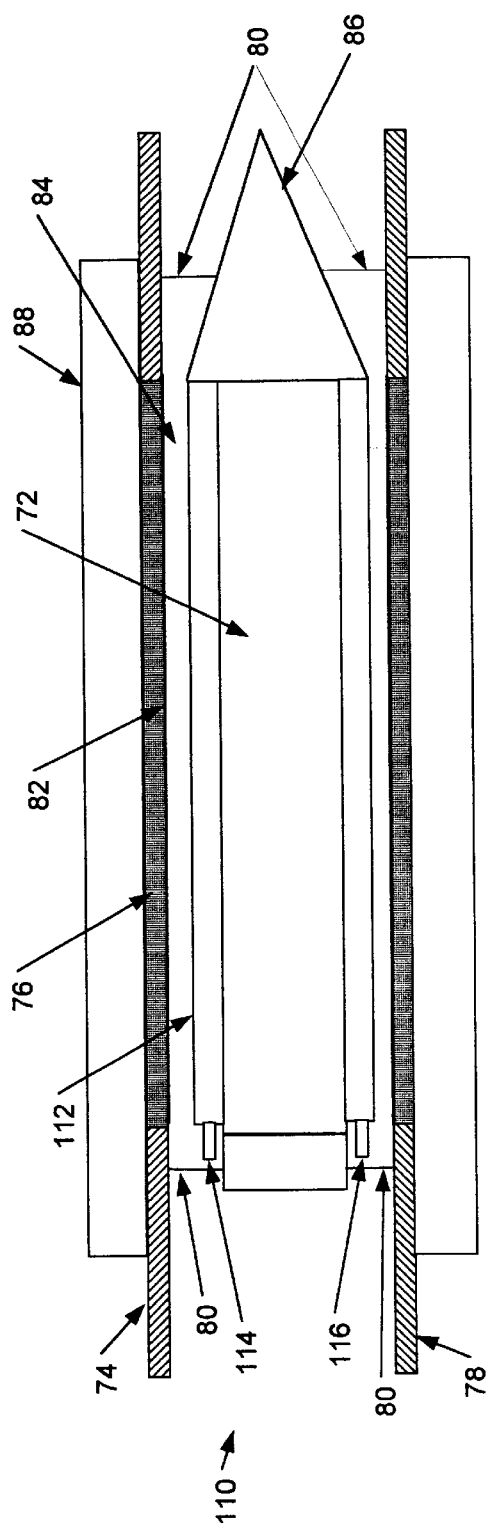

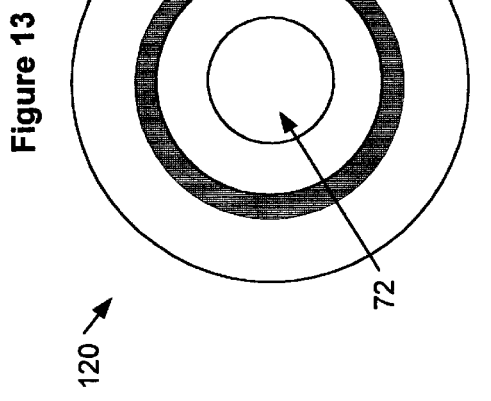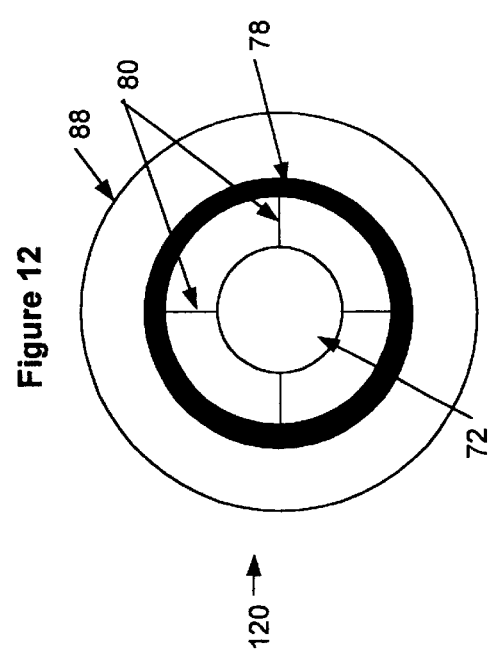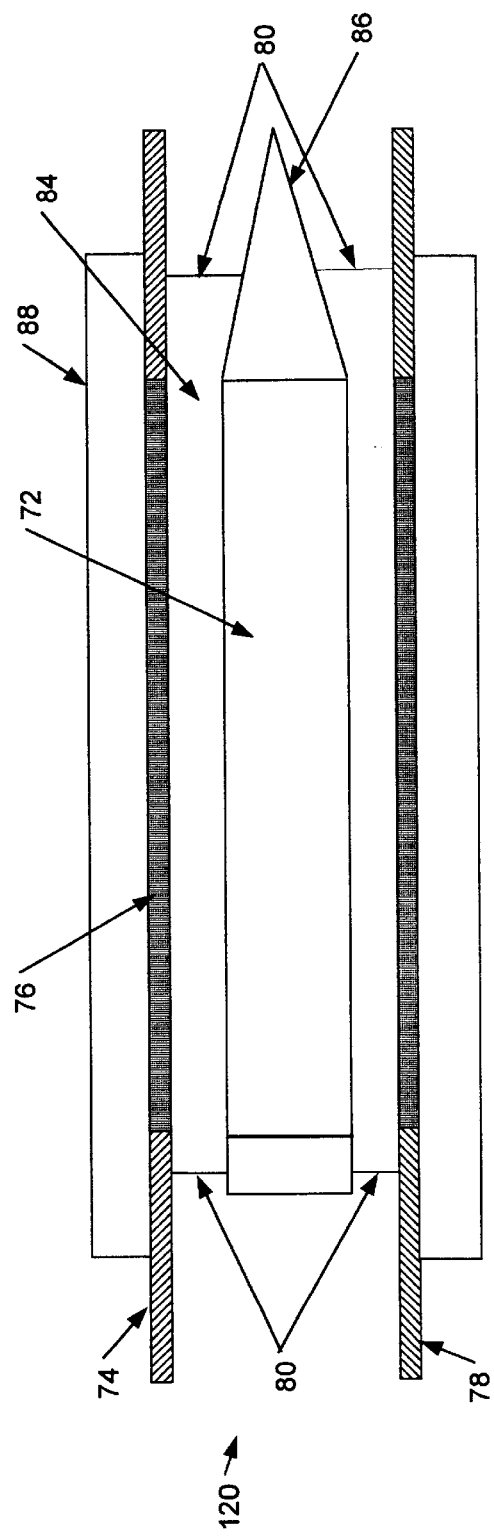

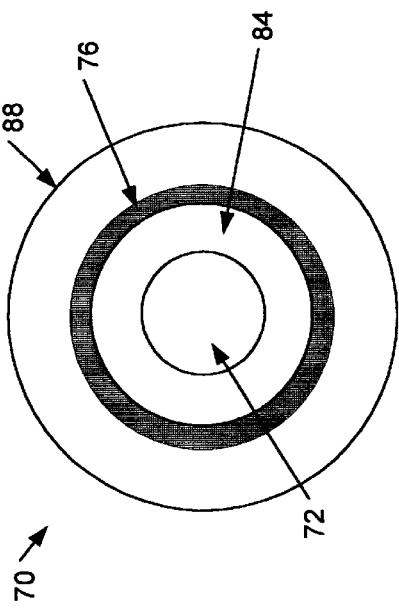
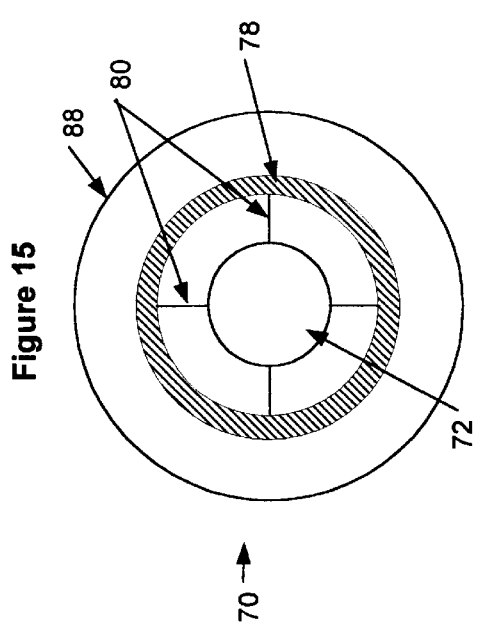
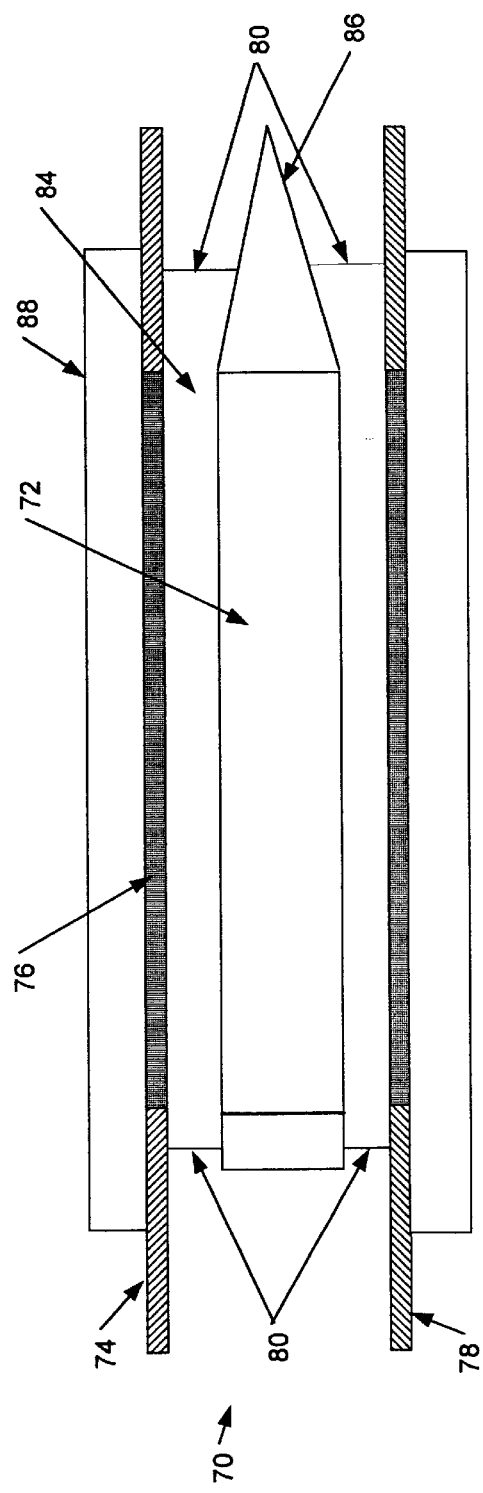

METHOD OF AND APPARATUS FOR MANUFACTURING METHANOL

CROSS-REFERENCE TO RELATED APPLICATIONS

This application is a continuation-in-part of prior application Ser. No. 09/370,945, filed Aug. 9, 1999, now U.S. Pat. No. 6,156,279, which is a divisional of prior application Ser. No. 09/224,394, filed Dec. 31, 1998, now U.S. Pat. No. 6,129,818, which is a continuation-in-part of prior application Ser. No. 09/058,494, filed Apr. 10, 1998, now U.S. Pat. Nos. 5,954,925 issued Sep. 21, 1999.

TECHNICAL FIELD

This invention relates generally to the manufacture of methanol, and more particularly to a method of and apparatus for manufacturing methanol from methane.

BACKGROUND OF THE INVENTION

Methanol, the simplest of the alcohols, is a highly desirable substance which is useful as a fuel, as a solvent, and as a feedstock in the manufacture of more complex hydrocarbons. In accordance with the method of methanol manufacture that is currently practiced in the petroleum industry, methane is first converted to synthesis gas, a mixture of carbon monoxide and hydrogen. The synthesis gas is then converted over an alumina-based catalyst to methanol. The formation of synthesis gas from methane is an expensive process.

As will be apparent, methane and methanol are closely related chemically. Methane comprises a major component of natural gas and is therefore readily available. Despite the advantages inherent in producing methanol directly from methane, no commercially viable system for doing so has heretofore been developed.

SUMMARY OF THE INVENTION

The present invention comprises a method of and apparatus for manufacturing methanol from methane which overcomes the foregoing and other deficiencies which have long since characterized the prior art. In one aspect, the method involves a semipermeable partition upon which a light-activated catalyst capable of producing hydroxyl radicals from water is deposited. Water is passed over the catalyst side of the porous surface and methane at a positive pressure is present on the opposite side of the surface. The catalyst is exposed to light while water is passed over the catalyst. The light-exposed catalyst reacts with the water molecules to form hydroxyl radicals. The methane gas is forced through the semipermeable partition forming small bubbles in the flowing water. The hydroxyl radicals in the water then undergo a free-radical reaction with the methane gas in the water to form methanol.

In accordance with the broader aspects of the invention there is generated a stream of sub-micron sized methane bubbles. Due to their extremely small size, the methane bubbles have an extremely large surface area which increases reaction efficiency. Smaller pores in the semipermeable partition facilitate the formation of smaller bubbles. Additionally, high relative velocity between the water and the catalytic surface aids in shearing the bubbles off the surface while they are still small.

In accordance with one embodiment of the invention, a porous tube has an exterior coating comprising a semiconductor catalyst. The porous tube is positioned within a glass tube and water is caused to continuously flow through the annular space between the two tubes. Methane is directed into the interior of the porous tube and is maintained at a pressure high enough to cause methane to pass into the water and prevent the flow of water into the interior of the tube. As the water passes over the porous tube, methane bubbles are continually sheared off of the sintered surface. The methane bubbles thus generated are sub-micron in size and then therefore present an extremely large surface area.

Electromagnetic radiation generated from a suitable source is directed through the glass tube and engages the semiconductor catalyst to generate hydroxyl radicals in the flowing water. The hydroxyl radicals undergo a free-radical reaction with the methane forming methanol, among other free-radical reaction products. Subsequently, the methanol is separated from the reaction mixture by distillation.

In accordance with another embodiment of the invention, a porous tube surrounds a tubular lamp. The inside diameter of the tube is larger than the outside diameter of the tubular lamp thereby providing an annulus between the tube and the lamp. Methane is directed inwardly through the porous tube and is thereby formed into submicron size bubbles and sheared by high relative velocity between the inside surface of the porous tube and water flowing in the annulus between the porous tube and the lamp. A photocatalytic layer may be placed on the interior surface of the porous tube for activation by light from the lamp.

BRIEF DESCRIPTION OF THE DRAWINGS

A more complete understanding of the invention may be had by reference to the following Detailed Description when taken in conjunction with the accompanying Drawings wherein:

FIG. 4 is a side view of an apparatus for manufacturing methane comprising a fourth embodiment of the invention;

FIG. 5 is an end view of the apparatus of FIG. 5;

FIG. 6 is a transverse sectional view of the apparatus of FIG. 4;

FIG. 7 is a diagrammatic illustration of a method and apparatus for manufacturing methane comprising the fourth embodiment of the invention;

FIG. 8 is a view similar to FIG. 4 illustrating an apparatus for manufacturing methane comprising a first alternative version of the fourth embodiment of the invention;

FIG. 9 is a view similar to FIG. 5 further illustrating the first alternative version of the fourth embodiment of the invention;

FIG. 10 is a view similar to FIG. 6 further illustrating the first alternative version of the fourth embodiment of the invention;

FIG. 11 is a view similar to FIG. 4 illustrating an apparatus for manufacturing methane comprising second and third alternative versions of the fourth embodiment of the invention;

FIG. 12 is a view similar to FIG. 5 further illustrating the second and third alternative versions of the fourth embodiment of the invention;

FIG. 13 is a view similar to FIG. 6 further illustrating the second and third alternative versions of the fourth embodiment of the invention;

FIG. 14 is a view similar to FIG. 4 further illustrating the invention;

FIG. 15 is a view similar to FIG. 5 further illustrating the invention; and

FIG. 16 is a view similar to FIG. 6 further illustrating the invention.

DETAILED DESCRIPTION

Figure 1:
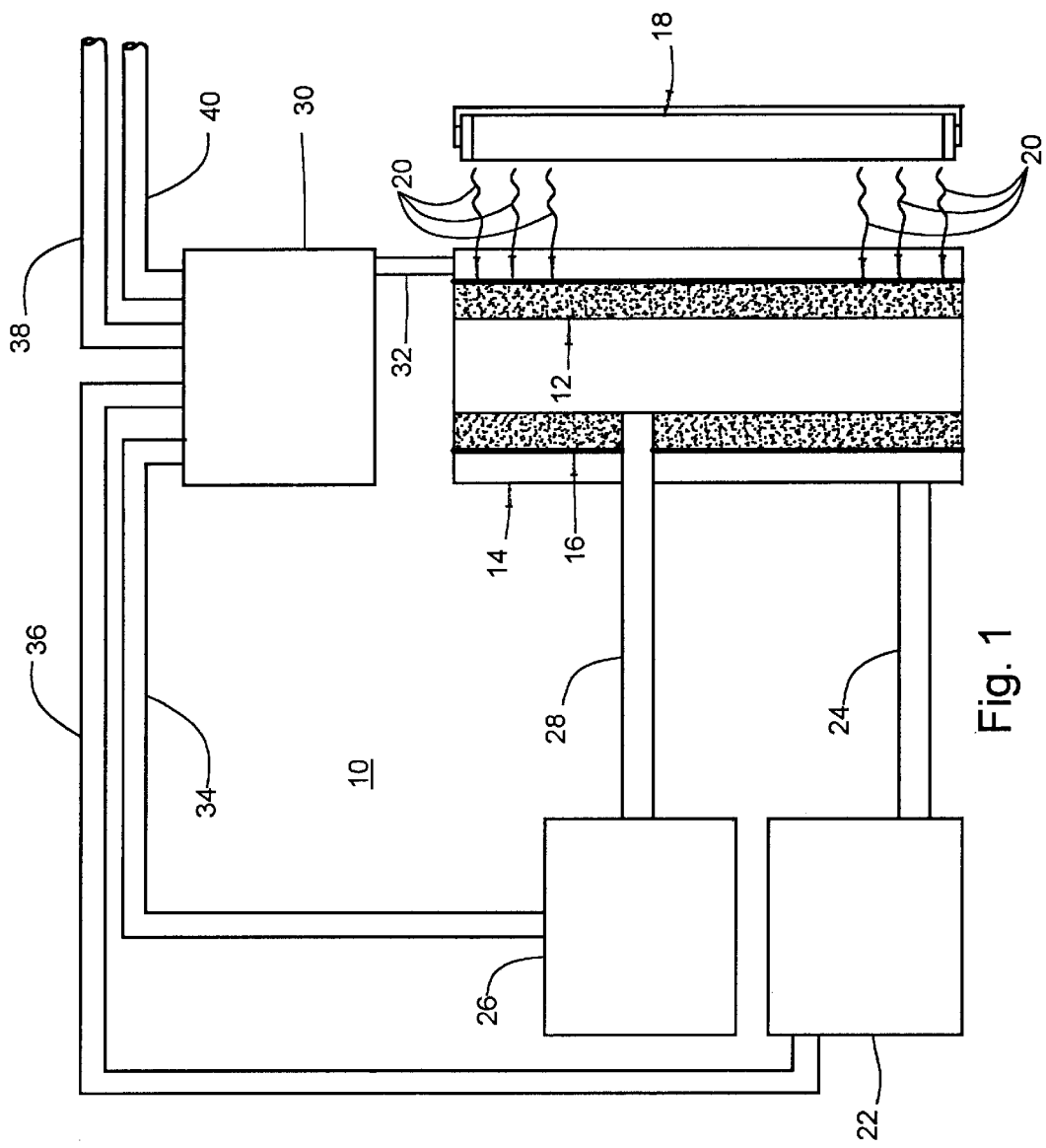
FIG. 1 is a diagrammatic illustration of a method and apparatus for manufacturing methane comprising a first embodiment of the present invention.

Referring now to the Drawings, and particularly to FIG. 1 thereof, there is shown an apparatus for manufacturing methanol 10 comprising a first embodiment of the invention. The apparatus 10 includes a porous tube 12 positioned within a glass tube 14. As illustrated in FIG. 1, both the porous tube 12 and the glass tube 14 comprise right circular cylinders with the tube 12 extending concentrically relative to the tube 14. Other geometrical configurations of and positional relationships between the porous tube 12 and the glass tube 14 may be utilized in accordance with the requirements of particular applications of the invention.

The porous tube 12 is characterized by pores or interstices having diameters of between about 0.1 microns and about 5 microns. In the case of round or near-round pores or interstices, the term "diameter" is used in its usual sense. In the case of substantially non-round pores or interstices, the term "diameter" means the major dimension thereof.

The porous tube 12 may be manufactured from steel, stainless steel, and numerous other metals; or from various ceramics; or from glass. When formed from metal, the porous tube 12 may be fabricated by sintering. Other well known manufacturing techniques may be utilized in the fabrication of the porous tube 12 in accordance with the requirements of particular applications of the invention.

The porous tube 12 has a semiconductor catalyst layer 16 formed on the exterior surface thereof. The catalyst layer 16 is preferably a titanium-based or a tungsten-based catalyst; however, it will be understood that any light-activated catalyst which forms hydroxyl radicals from water may be utilized in the practice of the invention, if desired.

The catalyst layer 16 has a thickness of between about 2 microns and about 100 microns. The catalyst layer 16 is further characterized by regularly spaced pores or interstices extending entirely through the catalyst layer and having diameters of between about 0.1 microns and about 1 micron.

A plurality of electromagnetic radiation sources 18 are positioned around the exterior of the glass tube 14, it being understood that while only one source 18 is illustrated in FIG. 1, in actual practice a plurality of sources 18 may be employed and disposed around the entire periphery of the tube 14. As illustrated by the waves 20 in FIG. 1, the sources 18 generate energy in the form of electromagnetic radiation which is directed through the glass tube 14 and onto the catalyst layer 16 formed on the exterior surface of the porous tube 12. By way of example, the sources 18 may comprise sources which generate electromagnetic radiation.

In the operation of the apparatus for manufacturing methanol 10, a quantity of water is received in a reservoir 22. Water from the reservoir 22 is directed into the annular space between the porous tube 12 and the glass tube 14 through piping 24. During the operation of the apparatus 10 water flows through the annulus between the tube 12 and the glass tube 14 on a continuous basis.

A quantity of methane is stored in a reservoir 26. In the operation of the apparatus 10, methane is directed from the reservoir 26 into the interior of the porous tube 12 through piping 28. The methane within the porous tube 12 is maintained at a pressure high enough to cause methane to pass through the walls of the porous tube 12 into the water and prevent the flow of water into the interior of the tube 12.

In the operation of the apparatus for manufacturing methanol 10, the water flowing through the annular space between the tube 12 and the glass tube 14 causes methane bubbles to be continuously stripped off surface of the catalyst layer 16. In this manner the size of the methane bubbles is maintained in the sub-micron range. The sub-micron size of the methane bubbles provides an enormous methane surface area which in turn results in unprecedented reaction efficiency.

As the sub-micron size methane bubbles are produced by the flow of water over the exterior surface of the porous tube 12, electromagnetic energy from the sources 18 continuously engages the catalyst layer 16 formed on the exterior of the tube 12. This generates hydroxyl radicals in the flowing water. The hydroxyl radicals cleave one or more of the carbon-hydrogen bonds in the methane thereby forming either molecules of hydrogen or molecules of water, depending upon the initiating radical, and methyl radicals. The methyl radicals combine either with the hydroxyl radicals to form methanol or with the hydrogen radicals to form methane.

Those skilled in the art will appreciate the fact that other chemical reactions are possible in the operation of the apparatus for manufacturing methanol 10. For example there exists the possibility of a methyl-methyl radical reaction, and also the possibility of a hydrogen-hydrogen radical reaction. Both of these possibilities are extremely remote due to the relatively low concentrations of methyl radicals and hydrogen radicals at any given time.

The water flowing from the annulus between the tube 12 and the glass tube 14 having the reaction products contained therein is directed to a distillation apparatus 30 through piping 32. The distillation apparatus 30 separates the outflow from the space between the tube 12 and the tube 14 into at least four streams, including a stream of unreacted methane 34 which is returned to the reservoir 26, a stream of water 36 which is returned to the reservoir 22, a stream of other reaction products 38 which are recovered, and a stream of methanol 40. The stream of other reaction products 38 may be further separated into its component parts, if desired.

The present invention further comprises a method of making methanol. In accordance with the method there is provided a continuously flowing stream of water. Sub-micron size bubbles of methane are continuously injected into the flowing water. Hydroxyl radicals are continuously generated from the water. The hydroxyl radicals cleave the hydrogen-carbon bonds of the methane to form methyl radicals. The methyl radicals combine with the hydroxyl radicals to form methanol.

In accordance with more specific aspects of the method, a porous tube having a semiconductor catalytic layer on the exterior surface thereof is positioned within a glass tube. Water is directed through the annulus between the porous tube and the glass tube, and methane is directed into the interior of the porous tube. The water flowing between the porous tube and the glass tube continuously strips sub-micron sized bubbles from the exterior surface of the catalytic layer.

Energy from electromagnetic radiation sources is directed through the glass tube and engages the catalytic surface on the exterior of the porous tube, thereby forming hydroxyl radicals from the flowing water. The hydroxyl radicals cleave one of the carbon-hydrogen bonds in the methane to form either molecules of hydrogen or molecules of water, and methyl radicals. The methyl radicals combine either with the hydroxyl radicals to form methanol or with the hydrogen radicals to form methane.

The use of an internal semipermeable partition cylinder is shown in FIG. 1. One skilled in the art would also recognize that a vast number of shapes and orientations could be used to accomplish the same purpose. For example, glass tube 14 does not need to be shaped as a tube in order to be functional as a housing. In fact, such a housing need only be partially transparent to electromagnetic radiation for the apparatus to function. Additionally, the orientation of the methane inside an inner tube with water between the inner tube and a housing is not required. One skilled in the art could envision a housing bisected by a semipermeable partition creating a water chamber and a methane chamber. The only requirements of such an embodiment is that the water chamber has a water source and a product outlet, which leads to a methanol isolation apparatus, preferably a distillation apparatus; the methane chamber has a methane source; the semipermeable partition has a catalytic layer that is exposed to light energy on the water side of the partition; and the semipermeable partition allows the penetration of methane bubbles that are sheared off by the relative movement of water in the water chamber.

Figure 2:
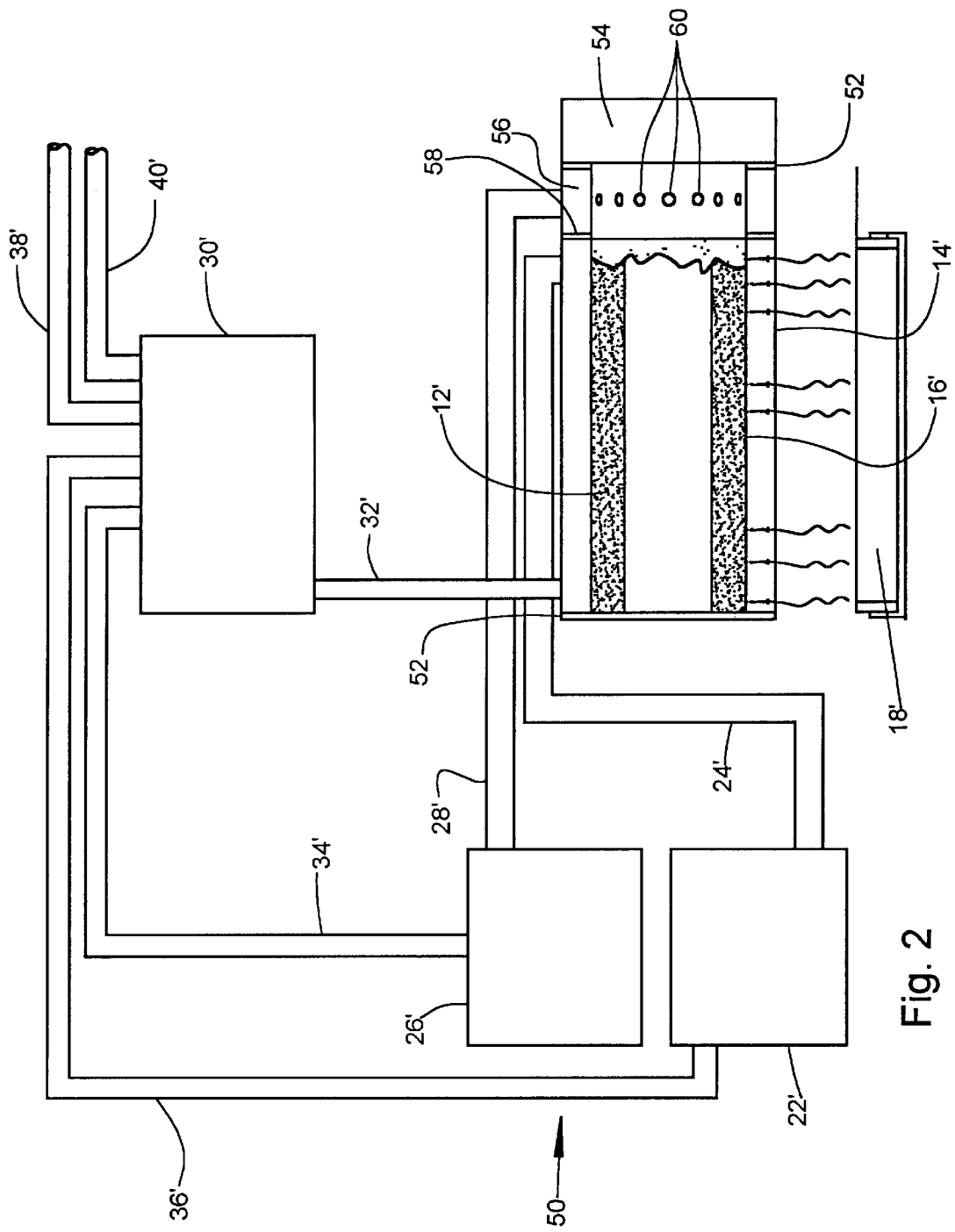
FIG. 2 is a diagrammatic illustration of a second embodiment of the apparatus of the present invention with a rotating porous tube.

Referring now to FIG. 2, there is shown an apparatus for manufacturing methanol comprising a second embodiment of the invention. The apparatus 50 comprises numerous component parts which are substantially identical in construction and function to the apparatus for manufacturing methanol 10 shown in FIG. 1 and described hereinabove in conjunction therewith. Such identical component parts are designated in FIG. 2 with the same reference numerals utilized in the description of the apparatus 10, but are differentiated therefrom by means of a prime (') designation.

In the apparatus for manufacturing methanol 50, the porous tube 12' is supported for rotation relative to the glass tube 14' by sealed bearings 52. Those skilled in the art will appreciate the fact that bearing/seal assemblies comprising separate components may be utilized in the practice of the invention, if desired.

A motor 54 is mounted at one end of the glass tube 14' and is operatively connected to the porous tube 12' to effect rotation thereof relative to the glass tube 14'. The glass tube 14' includes an end portion 56 which is isolated from the remainder thereof by a seal 58. The portion of the porous tube 12' extending into the end portion 56 of the glass tube 14' is provided with a plurality of uniform or nonuniform apertures 60.

In the operation of the apparatus for manufacturing methanol 50, methane is directed from the reservoir 26' through the piping 28' through the end portion 56 of the glass tube 14' and through the apertures 60 into the interior of the porous tube 12'. Water flows from the reservoir 22' through the piping 24' into the portion of the glass tube 14'that is isolated from the end portion 56 by the seal 58. Water flows out of the glass tube 14' through piping 32', to the distillation apparatus 30'.

The operation of the apparatus for manufacturing methanol 50 of FIG. 2 differs from the operation of the apparatus for manufacturing methanol 10 of FIG. 1 in that in the operation of the apparatus 50, the relative movement between the bubbles forming on the surface of the porous tube 12' and the water contained within the glass tube 14' is controlled by the motor 54 rather than the flow rate of the water as it passes through the glass tube 14'. This is advantageous in that it allows the porous tube 12' to be rotated at a relatively high velocity relative to the water contained within the glass tube 14', thereby assuring that sub-micron size bubbles will be sheared from the surface of the catalyst layer 16'. Meanwhile, the velocity of the water passing through the interior of the glass tube 14' can be relatively slow, thereby assuring a maximum number of sub-micron size bubbles entering the water per unit volume thereof.

Figure 3:
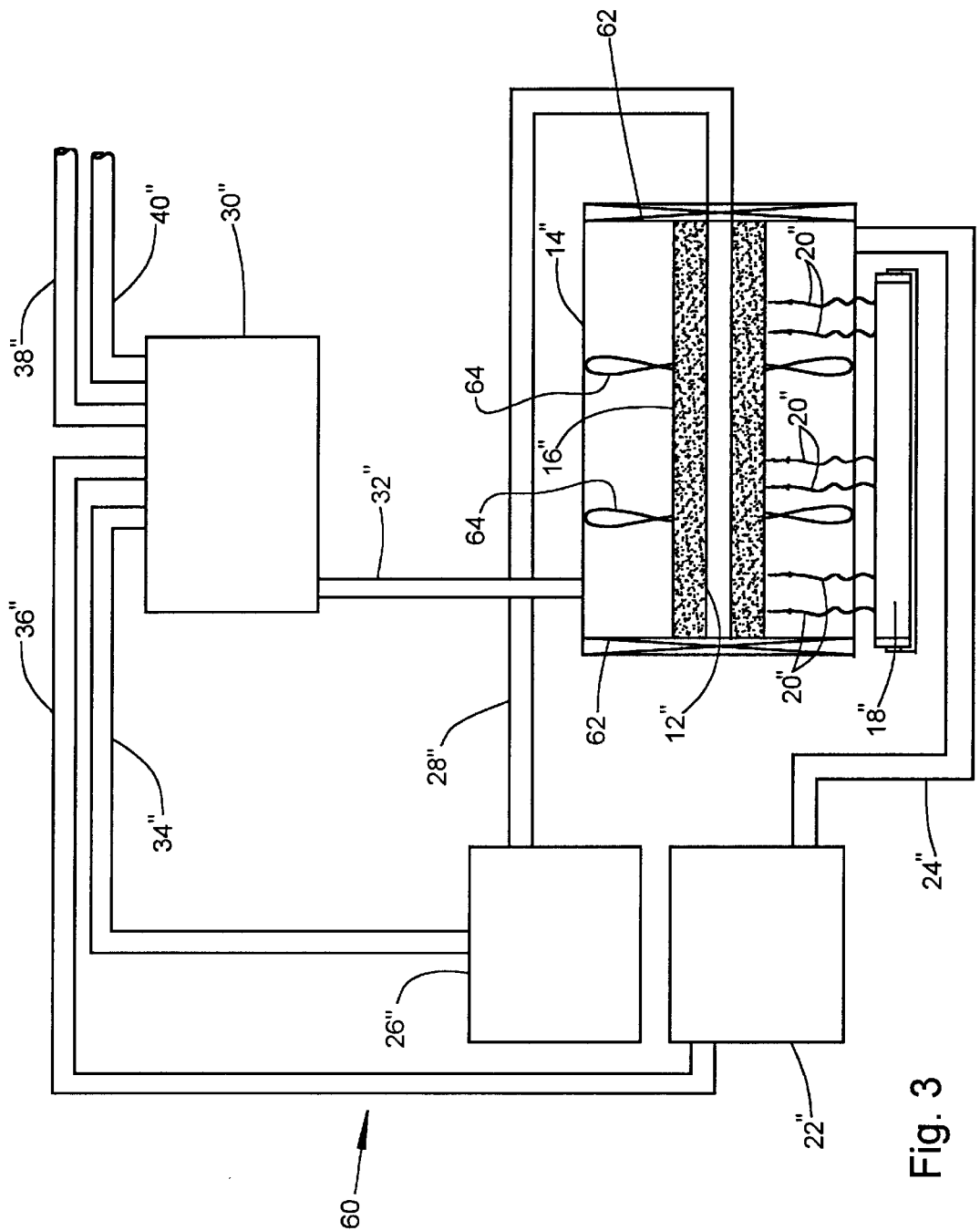
FIG. 3 is a diagrammatic illustration of a third embodiment of the apparatus of the present invention with a rotating porous tube with turbines.

An apparatus for manufacturing methanol comprising a third embodiment of the invention is illustrated in FIG. 3. The apparatus for manufacturing methanol 61 comprises numerous component parts which are substantially identical in construction and function to component parts of the apparatus for manufacturing methanol 10 illustrated in FIG. 1 and described hereinabove in conjunction therewith. Such identical component parts are designated in FIG. 3 with the same reference numerals utilized in the description of the apparatus 10, but are differentiated therefrom by means of a double prime (") designation.

The apparatus for manufacturing methanol 61 comprises a porous tube 12" which is supported for rotation relative to the glass tube 14" by sealed bearings 62. Those skilled in the art will appreciate the fact that the apparatus 61 may be provided with bearing/seal assemblies comprising separate components, if desired.

The porous tube 12" is provided with one or more turbines 64. The pitch of the turbines 64 is adjusted to cause the porous tube 12" to rotate at a predetermined speed in response to a predetermined flow rate of water through the glass tube 14".

Similarly to the apparatus for manufacturing methanol of FIG. 2, the use of the apparatus for manufacturing methanol 61 is advantageous in that the porous tube 12" can be caused to rotate relatively rapidly in response to a relatively low flow rate of water through the glass tube 14". This assures that sub-micron size bubbles will be stripped from the outer surface of the catalyst layer 16" and that a maximum number of bubbles will be received in the water flowing through the glass tube 14" per unit volume thereof. The use of the apparatus for manufacturing methanol 61 is particularly advantageous in applications of the invention wherein water flows through the system under the action of gravity, in that the use of the turbines 64 eliminates the need for a separate power source to effect rotation of the tube 12" relative to the glass tube 14".

Referring now to FIGS. 4, 5, and 6, there is shown an apparatus for manufacturing methanol 70 comprising a fourth embodiment of the invention. In accordance with the fourth embodiment, a tubular electromagnetic radiation source 72 extends coaxially within a tube 74 comprising a porous central portion 76 and solid, i.e., liquid and gas impervious, end portions 78. The source 72 is supported within the tube 74 by supports 80 which support the source 72 from the solid portions 78 of the tube 74. A photocatalytic layer 82 is formed on the interior surface of the porous central portion 76.

The central portion 76 of the tube 74 is characterized by pores or interstices having diameters of between about 0.1 microns and about 5 microns. In the case of round or near-round pores or interstices, the term "diameter" is used in its usual sense. In the case of substantially non-round pores or interstices, the term "diameter" means the major dimension thereof.

The catalyst layer 82 has a thickness of between about 2 microns and about 100 microns. The catalyst layer 82 is further characterized by regularly spaced pores or interstices extending entirely through the catalyst layer and having diameters of between about 0.1 micron and about 1 micron.

The inside diameter of the tube 74 is substantially larger than the outside diameter of the source 72 thereby providing an annulus 84 which facilitates the flow of water and/or other liquids around the exterior of the source 72 and across the inside surface of the porous portion 76 of the tube 74. Liquid flows through the annulus 84 from right to left (FIG. 4). The source 72 is provided with a conical end member 86 which facilitates liquid flow around the source 72 and through the annulus 84.

A gas impervious housing 88 is positioned around the porous portion 76 of the tube 74. In the operation of the apparatus 70, methane is maintained within the housing 88 at a pressure high enough to cause methane to flow through the porous portion 76 of the tube 74 and through the catalytic layer 82 while preventing the flow of liquid through the catalytic layer 82 and the porous portion 76 of the tube 74 and into the housing 88.

In the operation of the apparatus 70, a high relative velocity is established and maintained between the interior surface of the catalytic layer on interior of the tube 74 and the liquid flowing in the annulus 84 between the tube 74 and the source 72. The high relative velocity between the interior surface of the catalytic layer 82 and the liquid within the annulus 84 can be established by causing the liquid to flow rapidly through the annulus 84. Additionally, the tube 74 or at least the porous portion 76 thereof can be rotated, or reciprocated, or both rotated and reciprocated relative to the liquid flowing in the annulus 84, thereby further increasing the relative velocity between the interior surface of the sintered stainless steel portion 76 and the liquid.

The relatively smaller pores comprising the porous portion 76 of the tube 74 and the even smaller pores of the catalytic layer 82 facilitate the formation of very small bubbles of methane. The high relative velocity between the interior surface of the catalytic layer 82 and the liquid flowing through the annulus 84 shears the methane flowing through the catalytic layer 82 while the methane bubbles are of submicron size. In this manner the surface area of the methane entering the liquid flowing through the annulus 84 is greatly increased, resulting in a highly efficient reaction.

The characteristics of the photocatalytic material of the layer 82 are matched to the wave length spectrum of the electromagnetic radiation produced by the source 72 thereby causing the generation of hydroxyl radicals in the liquid flowing through the annulus 84. The hydroxyl radicals combine with the methane flowing through the porous portion 76 of the tube 74 and through the catalytic layer 82 to form methanol. The submicron size of the methane bubbles entering the liquid greatly increases the surface area of the methane which in turn greatly increases the efficiency of the reaction.

Referring to FIG. 7, there is shown a method of and apparatus for manufacturing methanol from methane 90 comprising the fourth embodiment of the invention. The method of and apparatus for manufacturing methanol 90 employs the apparatus for manufacturing methanol 70 which is illustrated in FIGS. 4, 5, and 6 and described hereandabove in conjunction therewith.

Methane from a source 92 is directed to the gas impervious housing of apparatus 70 through a line 94. Water from a source 96 is directed to the annulus of the apparatus 70 through a line 98. Reaction products from the apparatus 70 are directed to a distillation unit 100 through a line 102.

The distillation unit 100 separates the reaction products from the apparatus 70 into at least four streams. Unreacted methane is returned to the source 92 through a line 104. Water is returned to the source 96 through a line 106. Methanol produced by operation of the apparatus 70 is recovered from the distillation unit 100 through a line 108. Other reaction products produced by the operation of the distillation unit 100 are recovered through a line 109. The other reaction products from the line 109 may be further separated into component parts, if desired.

An apparatus 110 for manufacturing methanol comprising a first alternative version of the fourth embodiment of the invention is illustrated in FIGS. 8, 9, and 10. Many of the component parts of the apparatus 110 are identical in construction and function to component parts of the apparatus for manufacturing methanol 70 illustrated in FIGS. 4, 5, and 6 and described hereinabove in conjunction therewith. Such identical component parts are designated in FIGS. 8, 9, and 10 with the same reference numerals utilized in the description of the apparatus 70.

The apparatus for manufacturing methanol 110 differs from the apparatus for manufacturing methanol 70 in that the apparatus 110 is provided with a heat transfer cylinder or tube 112 surrounding the radiation source 72 and having an inlet 114 and an outlet 116. In the operation of the apparatus 110, a coolant liquid, for example, water, is directed through the tube 112 from the inlet 114 to the outlet 116 and is utilized to remove heat generated by operation of the source 72. The tube 112 is preferably provided with a partition (not shown) extending longitudinally thereof which forces liquid flowing from the inlet 114 through the tube 112 to the outlet 116 to travel the entire length of the tube 112.

The coolant liquid flowing through the tube 112 may be provided with a dye. If used, the dye is selected to control the wave length of the light passing from the source 72 to the catalytic layer 82. In this manner the efficiency of the catalytic reaction can be enhanced.

An apparatus 120 for manufacturing methanol comprising second and third alternative versions of the fourth embodiment of the invention is illustrated in FIGS. 11, 12, and 13. Many of the component parts of the apparatus 120 are identical in construction and function to component parts of the apparatus for manufacturing methanol 70 illustrated in FIGS. 4, 5, and 6 and described hereandabove in conjunction therewith. Such identical component parts are designated in FIGS. 11, 12, and 13 with the same reference numerals utilized in the description of the apparatus 70.

The apparatus 120 differs from the apparatus 70 illustrated in FIGS. 4, 5, and 6 and described hereandabove in conjunction therewith and from the apparatus 110 illustrated in FIGS. 8, 9, and 10 and described hereandabove in conjunction therewith in that the apparatus 120 does not employ a layer of photocatalytic material. In accordance with a second alternative version of the fourth embodiment of the invention, the apparatus 120 utilizes a source of electromagnetic radiation 72 which generates high frequency, low wave length radiation. It is known that high frequency, low wave length radiation has a sufficient energy to generate hydroxyl radicals from water without requiring the use of a photocatalyst. Therefore, in the practice of the second alternative version of the fourth embodiment of the invention, the use of photocatalytic material is dispensed with.

FIGS. 11, 12, and 13 also illustrate a third alternative version of the fourth embodiment of the invention. In accordance with the third alternative version of the fourth embodiment of the invention, the source 72 generates electromagnetic radiation. Particles comprising photocatalytic material are circulated through the annulus 84 between the source 72 and the porous section 76 of the tube 74 in the water flowing therethrough. The particles of photocatalytic material can be micro-porous, macro-porous, or non-porous in nature. The particles of photocatalytic material operate similarly to the layer of photocatalytic material 82 employed in the apparatus 70 and in the apparatus 110 in that upon actuation by radiation from the source 72 the photocatalytic material comprising the particles generates hydroxyl radicals in the water flowing through the annulus 84.

Referring again to FIG. 1, the tube 14 comprises a container which contains and directs the liquid, typically water, flowing through the annulus between the tube 14 and the tube 12. The tube 12 likewise comprises a container which receives methane. At least a portion of the tube 12 is porous so that the methane contained within the tube 12 is formed into sub-micron size bubbles and directed into the annulus between the tube 12 and the tube 14.

Referring to FIG. 4, the gas impervious housing 88 of the apparatus for manufacturing methanol 70 comprises a container which receives methane. The tube 74 comprises a container which receives and directs liquid, typically water, flowing through the annulus between the tube 74 and the source 72. The porous portion 76 of the tube 74 forms the methane contained by the gas impervious housing 88 into sub-micron size bubbles which are entrained in the flowing liquid.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method of manufacturing methanol from methane including the steps of:

providing a tubular source of electromagnetic radiation having a predetermined outside diameter;

providing a porous tube having an inside diameter larger than the outside diameter of the tubular radiation source;

positioning the porous tube coaxially with respect to and in axial alignment with the tubular radiation source thereby providing an annulus between the exterior of the tubular radiation source and the interior of the porous tube;

causing a liquid to flow through the annulus between the porous tube and the tubular radiation source;

directing methane through the porous tube and into the annulus between the porous tube and the tubular radiation source concurrently with the flow of liquid through the annulus;

causing a high relative velocity between the interior surface of the porous tube and the liquid flowing through the annulus between the porous tube and the tubular radiation source, thereby forming the methane flowing through the porous tube into submicron size bubbles;

utilizing radiation from the source to form hydroxyl radicals from the liquid flowing in the annulus between the porous tube and the tubular radiation source;

the hydroxyl radicals combining with the methane to form methanol;

providing a quantity of particles comprising a photocatalytic material;

entraining the particles of photocatalytic material in the liquid flowing through the annulus between the porous tube and the tubular radiation source;

thereby circulating the particles of photocatalytic material through the annulus between the porous tube and the tubular source.

2. The method according to claim 1 wherein the step of providing a quantity of particles of photocatalytic material is further characterized by providing a quantity of particles comprising a semiconductor photocatalytic material.

3. A method of manufacturing methanol from methane including the steps of:

providing a tubular source of electromagnetic radiation having a predetermined outside diameter;

providing a porous tube having an inside diameter larger than the outside diameter of the tubular radiation source;

positioning the porous tube coaxially with respect to and in axial alignment with the tubular radiation source thereby providing an annulus between the exterior of the tubular radiation source and the interior of the porous tube;

causing a liquid to flow through the annulus between the porous tube and the tubular radiation source;

directing methane through the porous tube and into the annulus between the porous tube and the tubular radiation source concurrently with the flow of liquid through the annulus;

causing a high relative velocity between the interior surface of the porous tube and the liquid flowing through the annulus between the porous tube and the tubular radiation source, thereby forming the methane flowing through the porous tube into submicron size bubbles;

utilizing radiation from the source to form hydroxyl radicals from the liquid flowing in the annulus between the porous tube and the tubular radiation source;

the hydroxyl radicals combining with the methane to form methanol and positioning a heat transfer apparatus within the annulus between the radiation source and the porous tube for removing heat caused by operation of the source.

4. The method of claim 3 further characterized by surrounding the tubular radiation source with a heat transfer tube and circulating a heat transfer medium through the heat transfer tube to remove heat generated by the operation of the source.

5. The method of claim 4 further characterized by mounting a layer of photocatalytic material on the interior of the porous tube for actuation by energy from the radiation source.

6. The method of claim 5 further characterized by circulating a dye through the heat transfer tube with the heat transfer medium thereby regulating the wave length of the energy from the radiation source which engages the layer of photocatalytic material.

\* \* \* \* \*